(12) United States Patent
Cropper

(10) Patent No.: US 7,481,225 B2
(45) Date of Patent: Jan. 27, 2009

(54) MEDICAL INSTRUMENT INCLUDING AN END EFFECTOR HAVING A MEDICAL-TREATMENT ELECTRODE

(75) Inventor: Michael S. Cropper, Edgewood, KY (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 626 days.

(21) Appl. No.: 11/043,516

(22) Filed: Jan. 26, 2005

(65) Prior Publication Data

US 2006/0167451 A1 Jul. 27, 2006

(51) Int. Cl.
*A61B 19/00* (2006.01)
(52) U.S. Cl. .......................................... 128/898; 606/41
(58) Field of Classification Search .................. 606/41, 606/50–52, 1, 45, 46; 128/898; 600/127, 600/104, 129, 146
See application file for complete search history.

(56) References Cited

U.S. PATENT DOCUMENTS

| | | | |
|---|---|---|---|
| 5,209,747 A * | 5/1993 | Knoepfler | 606/16 |
| 5,228,451 A | 7/1993 | Bales et al. | |
| 5,336,222 A | 8/1994 | Durgin, Jr. et al. | |
| 5,360,428 A | 11/1994 | Hutchinson, Jr. | |
| 5,403,311 A | 4/1995 | Abele et al. | |
| 5,482,054 A | 1/1996 | Slater et al. | |
| 5,496,317 A | 3/1996 | Goble et al. | |
| 5,582,617 A * | 12/1996 | Klieman et al. | 606/170 |
| 5,599,346 A | 2/1997 | Edwards et al. | |
| 5,702,390 A | 12/1997 | Austin et al. | |
| 5,849,011 A | 12/1998 | Jones et al. | |
| 5,957,863 A | 9/1999 | Koblish et al. | |
| 5,964,727 A | 10/1999 | Edwards et al. | |
| 6,096,037 A | 8/2000 | Mulier et al. | |
| 6,110,127 A * | 8/2000 | Suzuki | 606/170 |
| 6,663,639 B1 * | 12/2003 | Laufer et al. | 606/139 |
| 6,802,840 B2 | 10/2004 | Chin et al. | |
| 6,808,491 B2 | 10/2004 | Kortenbach et al. | |
| 6,837,884 B2 | 1/2005 | Woloszko | |
| 6,840,938 B1 * | 1/2005 | Morley et al. | 606/51 |
| 7,083,620 B2 * | 8/2006 | Jahns et al. | 606/51 |
| 7,118,569 B2 * | 10/2006 | Snay et al. | 606/46 |
| 2001/0009985 A1 | 7/2001 | Durgin et al. | |
| 2002/0072740 A1 | 6/2002 | Chandrasekaran et al. | |
| 2002/0078967 A1 | 6/2002 | Sixto et al. | |
| 2002/0099369 A1 | 7/2002 | Schulze | |
| 2002/0147447 A1 | 10/2002 | Long | |
| 2003/0014010 A1 | 1/2003 | Carpenter et al. | |
| 2003/0125728 A1 * | 7/2003 | Nezhat et al. | 606/41 |
| 2004/0030335 A1 * | 2/2004 | Zenati et al. | 606/51 |

(Continued)

*Primary Examiner*—John P Leubecker
*Assistant Examiner*—Victoria W Chen
(74) *Attorney, Agent, or Firm*—Victor Moreno

(57) ABSTRACT

A medical instrument includes a flexible sheath and an end effector. The sheath has a distal end. The end effector is attached to the sheath proximate the distal end and is insertable into a patient. The end effector includes opposing and retroflexed first and second jaws and includes at least one medical-treatment electrode supported by the second jaw. At least one of the first and second jaws is rotatable. In one implementation, the at-least-one medical-treatment electrode is operatively connectable to a medical radio-frequency (RF) generator. In one application, the end effector is insertable into the esophagus of a patient. In one employment, the first and second jaws are adapted to grasp a working end of a flexible tube of an endoscope.

2 Claims, 3 Drawing Sheets

U.S. PATENT DOCUMENTS

| | | |
|---|---|---|
| 2004/0073210 A1* | 4/2004 | Taniguchi et al. .............. 606/51 |
| 2004/0087940 A1* | 5/2004 | Jahns et al. .................... 606/41 |
| 2004/0097919 A1* | 5/2004 | Wellman et al. .............. 606/42 |
| 2004/0215188 A1 | 10/2004 | Mulier et al. |
| 2005/0090817 A1* | 4/2005 | Phan ........................... 606/41 |
| 2005/0113760 A1 | 5/2005 | Chachques et al. |
| 2005/0209564 A1 | 9/2005 | Bonner et al. |
| 2005/0256533 A1* | 11/2005 | Roth et al. ................... 606/167 |
| 2006/0041254 A1* | 2/2006 | Francischelli et al. ......... 606/41 |
| 2006/0178670 A1* | 8/2006 | Woloszko et al. .............. 606/48 |
| 2007/0010812 A1* | 1/2007 | Mittelstein et al. ............ 606/48 |
| 2007/0175488 A1* | 8/2007 | Cox et al. ................... 128/898 |

* cited by examiner

MEDICAL INSTRUMENT INCLUDING AN END EFFECTOR HAVING A MEDICAL-TREATMENT ELECTRODE

FIELD OF THE INVENTION

The present invention is related generally to medical instruments, and more particularly to a medical instrument including an end effector having a medical-treatment electrode.

BACKGROUND OF THE INVENTION

A known medical instrument includes a catheter having a distal end including an end effector having two medical-treatment electrodes. The distal end of the catheter is insertable into a working channel opening of an endoscope whose flexible tube has been inserted into the esophagus of a patient. A medical radio-frequency (RF) generator, which has been operatively connected to the electrodes, provides the electrodes with medical RF energy to stop bleeding in esophageal tissue of the patient.

Still, scientists and engineers continue to seek improved medical instruments which include end effectors having a medical-treatment electrode.

SUMMARY

A first expression of an embodiment of a medical instrument includes a flexible sheath and an end effector. The sheath has a distal end. The end effector is attached to the sheath proximate the distal end and is insertable into a patient. The end effector includes opposing and retroflexed first and second jaws and includes at least one medical-treatment electrode supported by the second jaw. At least one of the first and second jaws is rotatable.

Several benefits and advantages are obtained from the first expression of the embodiment of the invention. In one application, the end effector is inserted into the esophagus or the stomach of a patient with the first and second jaws in a more-closed position, and patient tissue is medically treated with the at-least-one medical-treatment electrode with the jaws in a more-opened position with the second jaw pressed against the patient tissue. In another application, the end effector is inserted into the esophagus or the stomach of a patient in a more-closed position, and patient tissue is medically treated with the at-least-one medical-treatment electrode with the jaws grasping the distal end of a flexible tube of an endoscope with the endoscope being used to bend the distal end of the flexible tube to move the second jaw against the patient tissue.

DETAILED DESCRIPTION

Figure 1:
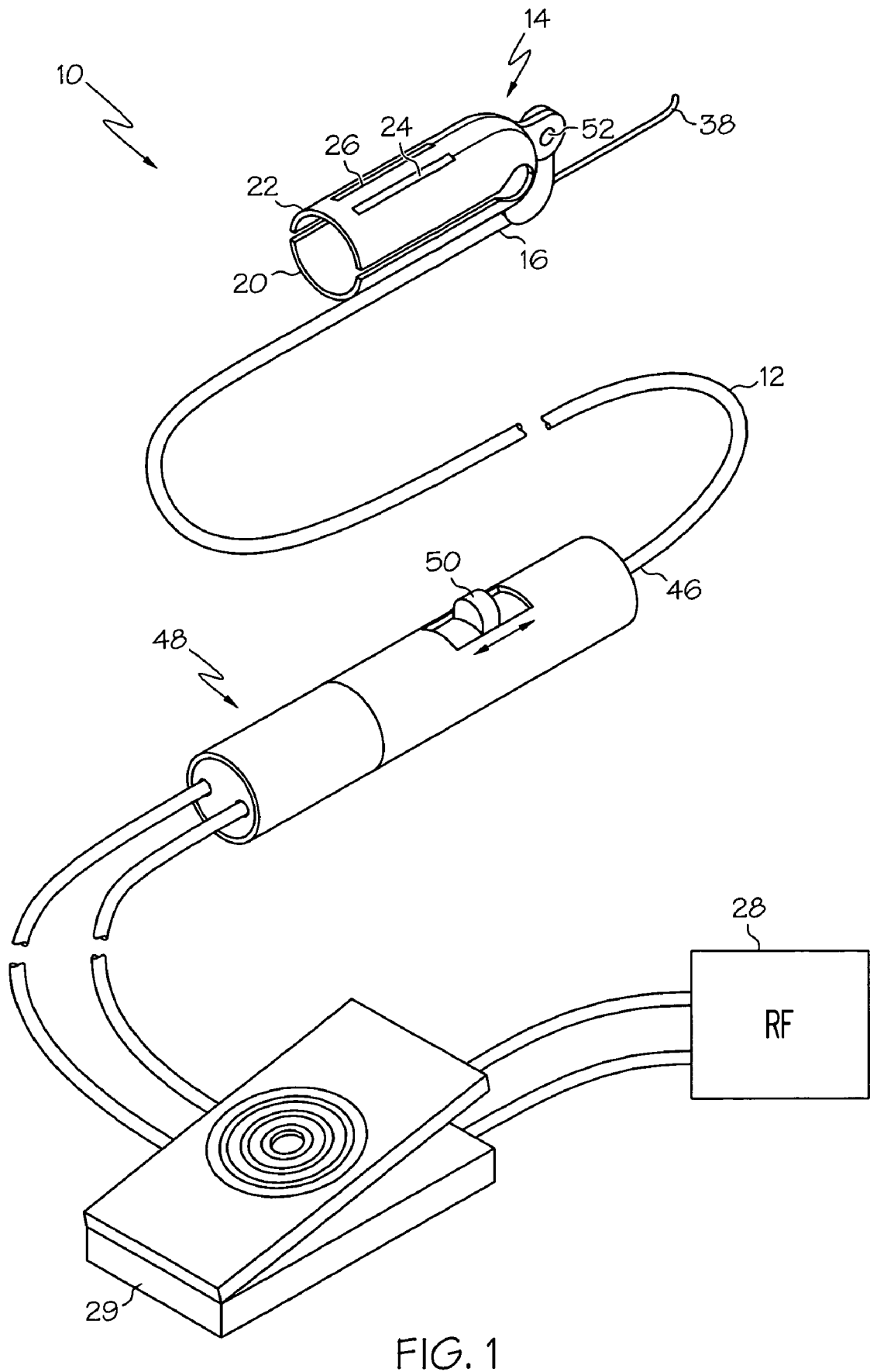
FIG. 1 is a schematic, perspective view of an embodiment of a medical instrument of the invention, wherein the end effector of the medical instrument is shown attached to a guide wire (only the distal portion of which is shown)

Before explaining the embodiment of the present invention in detail, it should be noted that the embodiment is not limited in its application or use to the details of construction and arrangement of parts and steps illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is further understood that any one or more of the following-described expressions of the embodiment, examples, etc. can be combined with any one or more of the other following-described expressions of the embodiment, examples, etc.

An embodiment of a medical instrument 10 of the invention is shown in FIGS. 1-5. A first expression of the embodiment of FIGS. 1-5 is for a medical instrument 10 including a flexible sheath 12 and an end effector 14. The sheath 12 has a distal end 16. The end effector 14 is attached to the sheath 12 proximate the distal end 16 and is insertable into a patient 18. The end effector 14 includes opposing and retroflexed first and second jaws 20 and 22 and includes at least one medical-treatment electrode 24 and 26 supported by the second jaw 22. At least one of the first and second jaws 20 and 22 is rotatable.

In one implementation of the first expression of the embodiment of FIGS. 1-5, the at-least-one medical-treatment electrode 24 and 26 includes two medical-treatment electrodes 24 and 26 operatively connectable to a medical radio-frequency (RF) generator 28 (such as through a foot switch 29). In one variation, the two medical-treatment electrodes 24 and 26 are operated in a bipolar manner. In another variation (or in a different implementation having only one electrode), the two (or one) medical-treatment electrodes 24 and 26 are operated in a monopolar manner.

Figure 2:
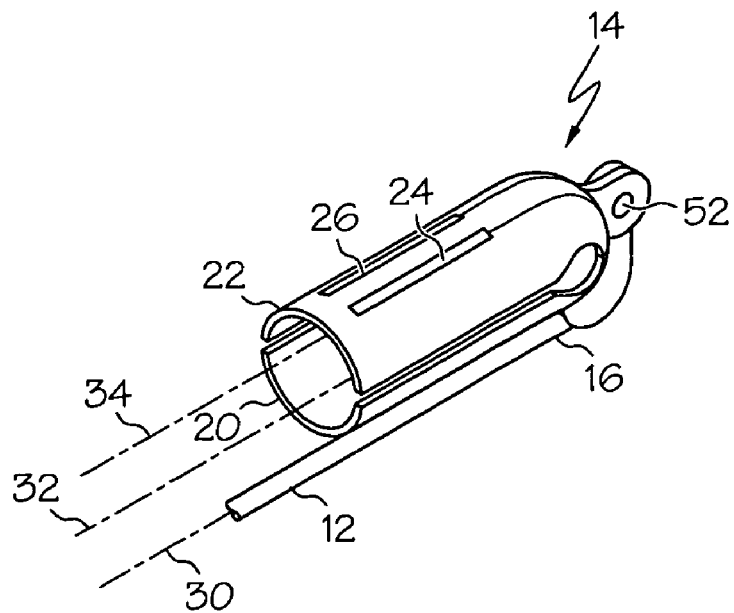
FIG. 2 is a schematic, perspective view of the end effector and the distal end portion of the sheath of the medical instrument of FIG. 1 with the first and second jaws in a more-closed position and with the guide wire removed.
Figures 3, 4:
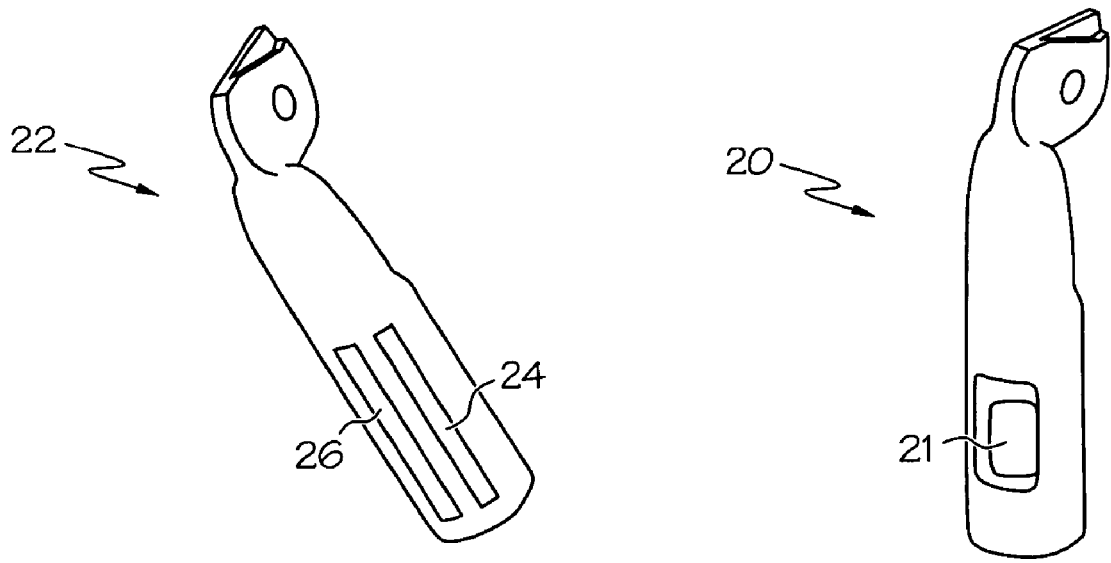
FIG. 3 is a perspective view of the outer surface of the second jaw of the end effector of FIG. 1 showing two medical-treatment electrodes supported by the second jaw.
FIG. 4 is a perspective view of the outer surface of the first jaw of the end effector of FIG. 1 showing a through hole in the first jaw.

In one arrangement of the first expression of the embodiment of FIGS. 1-5, the sheath 12 has a substantially straight centerline 30 when the sheath 12 is disposed substantially straight, the first jaw 20 has a longitudinally-extending first centerline 32, and the second jaw 22 has a longitudinally-extending second centerline 34. In this arrangement, when the at-least-one of the first and second jaws 20 and 22 is rotated to a position (which is a more-closed position) with the second jaw 22 proximate the first jaw 20 (as shown in FIG. 2), the first and second centerlines 32 and 34 are substantially parallel to the substantially straight centerline 30 with the first centerline 32 disposed between the second centerline 34 and the substantially straight centerline 30. It is noted that in the more-closed position, the opposing first and second jaws 20 and 22, being retroflexed, point back toward the proximal end 46 of the sheath 12 when the sheath 12 is disposed substantially straight and parallel to the first and second jaws 20 and 22.

Figure 5:
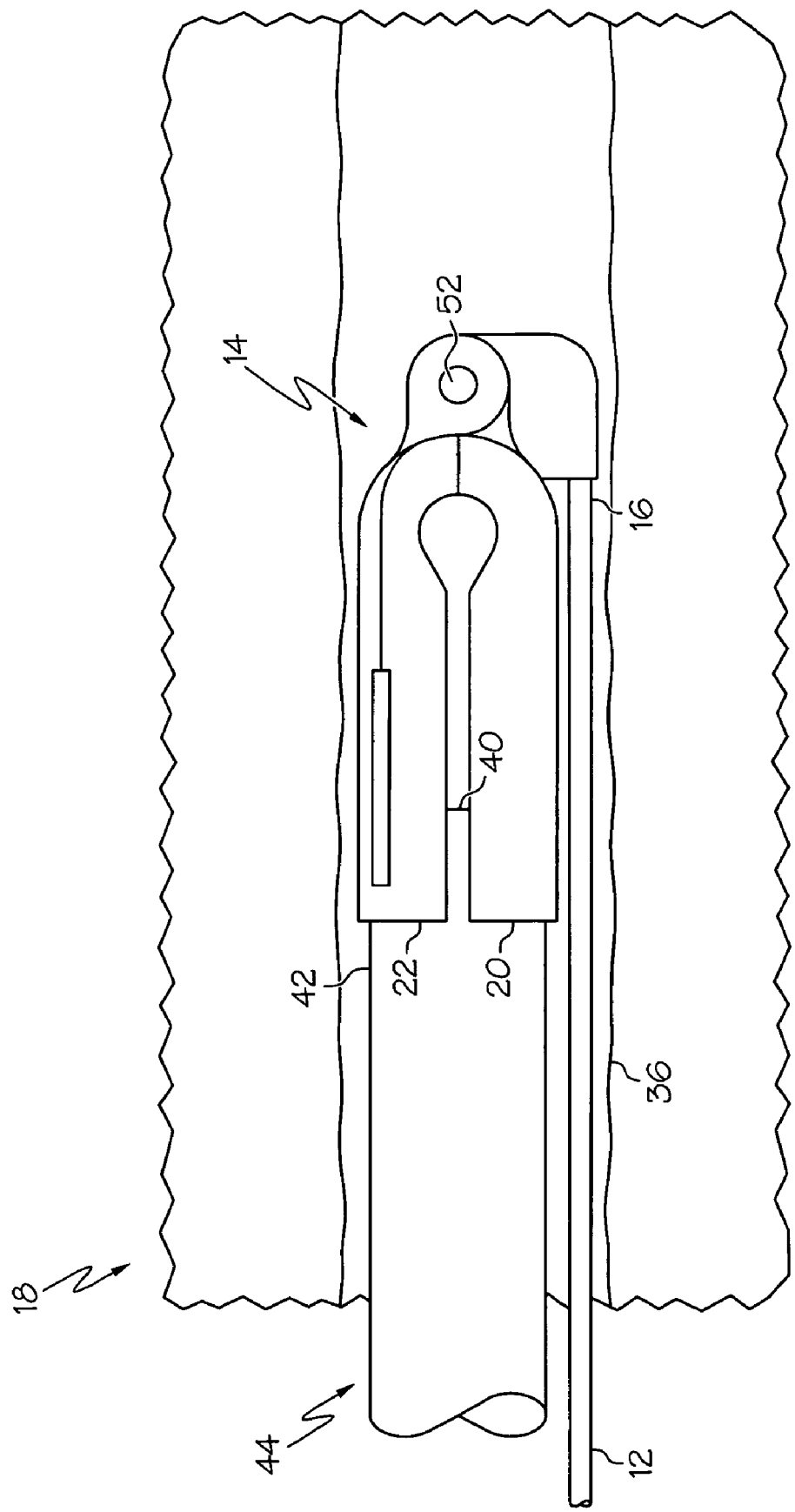
FIG. 5 is a schematic, side-elevational view of the end effector and the distal end portion of the sheath both disposed in the esophagus of a patient with the first and second jaws of the end effector grasping the distal end of a flexible tube of an endoscope.

In one application of the first expression of the embodiment of FIGS. 1-5, the end effector 14 is insertable into the esophagus 36 of the patient 18. In one utilization, one of the sheath 12 and the end effector 14 is operatively attachable to a guide wire 38. In one employment, the first and second jaws 20 and 22 are adapted to grasp a working end 40 of a flexible tube 42 of an endoscope 44 (only the flexible tube portion of which is shown in FIG. 5).

In one enablement of the first expression of the embodiment of FIGS. 1-5, the first jaw 20 has a through hole 21 adapted to receive therein patient tissue when the first and second jaws 20 and 22 grasp the working end 40 of the flexible tube 42 of an endoscope 44 and when the endoscope 44 is used to apply suction to the working end 40. In one example, when the end effector 14 is inserted into the esophagus 36 of a patient 18, when the first and second jaws 20 and 22 grasp the working end 40 of the flexible tube 42 of the endoscope 44, and when the endoscope 44 is used to apply suction to the working end 40, esophageal tissue surrounding the first jaw 20 is drawn into the through hole 21 in the first jaw 20 and into a chamber formed between the first and second jaws 20 and 22. This tightens the esophageal tissue surrounding the second jaw 22 into more intimate contact with the at-least-one medical-treatment electrode 24 and 26 which reduces charring of patient tissue, which improves non-visual monitoring of tissue treatment, and which improves hemostasis.

In one construction of the first expression of the embodiment of FIGS. 1-5, the second jaw 22 is substantially transparent. In one variation, the first jaw 20 also is substantially transparent. In one modification, the first and second jaws 20 and 22 comprise, consist essentially of, or consist of substantially-clear polycarbonate. In the same or a different modification, the first and second jaws 20 and 22 are substantially rigid. In one utilization, a compliant end cap portion, not shown, is attached to each of the jaws 20 and 22 to cushion their grasp (and create a better suction seal) on the working end 40 of the flexible tube 42 of the endoscope 44. In one example, the at-least-one medical-treatment electrode 24 and 26 is a copper electrode which has been nickel plated and then gold plated. In the same or a different example, the at-least-one medical-treatment electrode 24 and 26 includes two electrodes 24 and 26 bonded to a substantially transparent flexible substrate, not shown, (such as a substrate comprising, consisting essentially of, or consisting of polyester) which is attached to the second jaw 22. Having substantially transparent jaws 20 and 22 and substrates allows an endoscope 44 to be used to visually monitor the patient tissue between the two electrodes 24 and 26 during treatment, as can be appreciated by the artisan. In one enablement, electrical leads, not shown, are attached to the electrodes 24 and 26 and extend in the wall of the sheath 12. In the same or a different enablement, suction holes (only through hole 21 is shown) in the jaws 20 and 22 and the substrate provide, through endoscopic suction, more intimate contact of the patient tissue with the electrodes 24 and 26.

In one design of the first expression of the embodiment of FIGS. 1-5, the cross-sectional area of the closed jaws 20 and 22 at their free ends is less than that at their pivot and less than that of the working end 40 of the flexible tube 42 of the endoscope 44 to facilitate removal of the end effector 14 from the patient 18. In one variation, when the jaws 20 and 22 are proximate each other in a position where their centerlines 32 and 34 are substantially parallel, the cross-sectional area of the jaws 20 and 22 is substantially equal to that of the working end 40 of the flexible tube 42 of the endoscope 44.

In one extension of the first expression of the embodiment of FIGS. 1-5, the sheath 12 includes a proximal end 46, and the medical instrument 10 also includes a handle 48 attached to the proximal end 46. In one variation, the handle 48 includes a user-controlled actuator 50 operatively connected to the at-least-one of the first and second jaws 20 and 22 to rotate the at-least-one of the first and second jaws 20 and 22. In one modification, a push/pull rod, not shown, operatively connects the user-controlled actuator 50 to the at-least-one of the first and second jaws 20 and 22.

A first method for medically treating patient tissue uses the medical instrument 10 of the first expression of the embodiment of FIGS. 1-5 and includes several steps. One step includes inserting the end effector 14 into the mouth of a patient 18 and translating the end effector 14 to the esophagus 36 or the stomach of the patient 18. Another step includes inserting a working end 40 of a flexible tube 42 of an endoscope 44 into the mouth of the patient 18 and translating the working end 40 of the flexible tube 42 to the esophagus 36 or the stomach of the patient 18. Another step includes grasping the working end 40 of the flexible tube 42 with the first and second jaws 20 and 22. Another step includes using the endoscope 44 to bend the working end 40 of the flexible tube 42 to move the second jaw 22 against patient tissue of the esophagus 36 or the stomach. Another step includes medically treating the patient tissue using the at-least-one medical-treatment electrode 24 and 26.

In one utilization of the first method, a guide wire 38 is inserted into the patient through a working channel opening, not shown, of the endoscope 44 for placement in the esophagus 36 or the stomach. After removal of the flexible tube 42 of the endoscope 44 from the patient 18, the sheath 12 or the end effector 14 is attached to the guide wire 38 before the step of inserting the end effector 14 into the mouth of a patient 18 and translating the end effector 14 to the esophagus 36 or the stomach of the patient 18. In one variation, after the end-effector insertion step, the flexible tube 42 of the endoscope 44 is again inserted into the patient for visual verification that the electrodes 24 and 26 are at the desired location before removing the guide wire 38 from the patient 18. In one modification, after removal of the guide wire 38 from the patient 18, the endoscope 44 is used to visually monitor patient tissue between the electrodes 24 and 26 during medical treatment.

In one medical procedure, the at-least-one medical-treatment electrode 24 and 26 is used to ablate patient tissue to shallow depths below the tissue surface. In one example, the medical instrument 10 is used to treat Barrett's disease on the inner lining of the esophagus 36.

A second expression of the embodiment of FIGS. 1-5 is for a medical instrument 10 including a flexible sheath 12 and an end effector 14. The sheath 12 has a distal end 16. The end effector 14 is attached to the sheath 12 proximate the distal end 16 and is insertable into a patient 18. The end effector 14 includes opposing and retroflexed first and second jaws 20 and 22 and includes at least one medical-treatment electrode 24 and 26 supported by the second jaw 22. The second jaw 22 is rotatable.

A second method for medically treating patient tissue uses the medical instrument 10 of the second expression of the embodiment of FIGS. 1-5 and includes several steps. One step includes inserting the end effector 14 into the mouth of a patient 18 and translating the end effector 14 to the esophagus 36 or the stomach of the patient 18. Another step includes rotating the second jaw 22 against patient tissue of the esophagus 36 or the stomach. Another step includes medically treating the patient tissue using the at-least-one medical-treatment electrode 24 and 26.

It is noted that the implementations, arrangements, applications, etc of the first expression of the embodiment of FIGS. 1-5 are equally applicable to the second expression of the embodiment of FIGS. 1-5.

A third expression of the embodiment of FIGS. 1-5 is for a medical instrument 10 including a flexible sheath 12 and an end effector 14. The sheath 12 has a distal end 16. The end effector 14 is attached to the sheath 12 proximate the distal end 16 and is insertable into a patient 18. The end effector 14 includes opposing and retroflexed first and second jaws 20 and 22 and includes at least one medical-treatment electrode 24 and 26 supported by the second jaw 22. The first and second jaws 20 and 22 are rotatable.

It is noted that the implementations, arrangements, applications, methods, etc of the first expression of the embodiment of FIGS. 1-5 are equally applicable to the third expression of the embodiment of FIGS. 1-5.

In one configuration of any one or more or all of the first, second, and third expressions of the embodiment of FIGS. 1-5, the rotation of one or both of the first and second jaws 20 and 22 is about a pivot axis 52 which is aligned substantially perpendicular to the first and second centerlines 32 and 34. Mechanisms able to rotate one or both of the first and second jaws 20 and 22 are within the ordinary level of skill of those knowledgeable about medical instruments.

Several benefits and advantages are obtained from the first expression of the embodiment of the invention. In one application, the end effector is inserted into the esophagus or the stomach of a patient with the first and second jaws in a more-closed position, and patient tissue is medically treated with the at-least-one medical-treatment electrode with the jaws in a more-opened position with the second jaw pressed against the patient tissue. In another application, the end effector is inserted into the esophagus or the stomach of a patient in a more-closed position, and patient tissue is medically treated with the at-least-one medical-treatment electrode with the jaws grasping the distal end of a flexible tube of an endoscope with the endoscope being used to bend the distal end of the flexible tube to move the second jaw against the patient tissue.

While the present invention has been illustrated by a description of several expressions of an embodiment and implementations, arrangements, etc. thereof, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended Claims.

What is claimed is:

1. A method for medically treating patient tissue using a medical instrument, wherein the medical instrument includes a flexible sheath having a distal end and an end effector attached to the sheath proximate the distal end and insertable into a patient, wherein the end effector includes opposing and retroflexed first and second jaws and includes at least one medical-treatment electrode supported by the second jaw, wherein at least one of the first and second jaws is rotatable, and wherein the method includes the steps of:
   a) inserting the end effector into the mouth of a patient and translating the end effector to the esophagus or the stomach of the patient;
   b) inserting a working end of a flexible tube of an endoscope into the mouth of the patient and translating the working end of the flexible tube to the esophagus or the stomach of the patient;
   c) grasping the working end of the flexible tube with the first and second jaws;
   d) using the endoscope to bend the working end of the flexible tube to move the second jaw against patient tissue of the esophagus or the stomach; and
   e) medically treating the patient tissue using the at-least-one medical-treatment electrode.

2. A method for medically treating patient tissue using a medical instrument, wherein the medical instrument includes a flexible sheath having a distal end and an end effector attached to the sheath proximate the distal end and insertable into a patient, wherein the end effector includes opposing and retroflexed first and second jaws and includes at least one medical-treatment electrode supported by the second jaw, wherein the second jaw is rotatable, and wherein the method includes the steps of:
   a) inserting the end effector into the mouth of a patient and translating the end effector to the esophagus or the stomach of the patient;
   b) inserting a working end of a flexible tube of an endoscope into the mouth of the patient and translating the working end of the flexible tube to the esophagus or the stomach of the patient;
   c) grasping the working end of the flexible tube with the first and second jaws;
   d) using the endoscope to bend the working end of the flexible tube to move the second jaw against patient tissue of the esophagus or the stomach; and
   e) medically treating the patient tissue using the at-least-one medical-treatment electrode.

* * * * *